United States Patent
Ohta et al.

(10) Patent No.: US 10,440,949 B2
(45) Date of Patent: *Oct. 15, 2019

(54) AQUEOUS AGROCHEMICAL SUSPENSION COMPOSITION AND DISPERSAL METHOD THEREFOR

(71) Applicants: KUMIAI CHEMICAL INDUSTRY CO., LTD., Tokyo (JP); NIPPON SODA CO., LTD., Tokyo (JP)

(72) Inventors: Yuichiro Ohta, Tokyo (JP); Toshinobu Yamazaki, Tokyo (JP)

(73) Assignees: KUMIAI CHEMICAL INDUSTRY CO., LTD., Tokyo (JP); NIPPON SODA CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/778,000

(22) PCT Filed: Nov. 28, 2016

(86) PCT No.: PCT/JP2016/085219
§ 371 (c)(1),
(2) Date: May 22, 2018

(87) PCT Pub. No.: WO2017/094677
PCT Pub. Date: Jun. 8, 2017

(65) Prior Publication Data
US 2018/0332843 A1  Nov. 22, 2018

Related U.S. Application Data

(63) Continuation of application No. PCT/JP2016/085219, filed on Nov. 28, 2016.

(30) Foreign Application Priority Data
Nov. 30, 2015  (JP) .................................. 2015-234179

(51) Int. Cl.
| A01N 25/00 | (2006.01) |
| A01N 25/04 | (2006.01) |
| A01N 47/10 | (2006.01) |
| A01N 47/12 | (2006.01) |
| A01N 25/30 | (2006.01) |

(52) U.S. Cl.
CPC ............ *A01N 25/04* (2013.01); *A01N 25/00* (2013.01); *A01N 25/30* (2013.01); *A01N 47/12* (2013.01); *A01N 47/10* (2013.01)

(58) Field of Classification Search
CPC ............................... A01N 47/10; A01N 47/12
USPC .................... 514/238.8, 241, 252.1
See application file for complete search history.

(56) References Cited

U.S. PATENT DOCUMENTS

| 6,812,229 | B1 | 11/2004 | Ozaki et al. |
| 2011/0233812 | A1 | 9/2011 | Fujita et al. |
| 2014/0171319 | A1 | 6/2014 | Schnabel et al. |
| 2018/0343866 | A1 | 12/2018 | Yamazaki et al. |

FOREIGN PATENT DOCUMENTS

| CN | 101773122 | | 7/2010 |
| CN | 104996450 | | 10/2015 |
| EP | 0 253 682 | | 1/1988 |
| EP | 3 384 772 | | 10/2018 |
| JP | 52-110833 | | 9/1977 |
| JP | 58-177903 | | 10/1983 |
| JP | 59-7101 | | 1/1984 |
| JP | 63-27401 | | 2/1988 |
| JP | 1-258603 | | 10/1989 |
| JP | 2001-106666 | | 4/2001 |
| JP | 2002-193701 | | 7/2002 |
| JP | 2002-363005 | | 12/2002 |
| JP | 2003-34603 | | 2/2003 |
| JP | 2004-345981 | | 12/2004 |
| JP | 2006-104097 | | 4/2006 |
| JP | 2007-314515 | | 12/2007 |
| JP | 2009137861 | A * | 6/2009 |
| WO | 2010/064513 | | 6/2010 |
| WO | 2013/017402 | | 2/2013 |

OTHER PUBLICATIONS

JP 2009137861 A, Okada et al., (2009), English-translated abstract.*
International Search Report dated Jan. 17, 2017 in International Application No. PCT/JP2016/085219.
Kenichi Kida, "Agchem Age", No. 195, Nippon Soda Co., Ltd., Dec. 2013, pp. 12-17.
Extended European Search Report dated Mar. 25, 2019 in corresponding European Patent Application No. 16870614.1.
Ansgar Behler, "Polycarboxylate—RÖMPP, Thieme", Römpp, p. 1, 2005.
Takagaki et al., "Disease-controlling effect of a novel fungicide pyribencarb against Botrytis cinerea", Journal of Pesticide Science, vol. 35, No. 1, pp. 10-14, 2010.
Chinese Office Action issued in corresponding Chinese Patent Application 201680070002.5 dated May 7, 2019, with English translation.

* cited by examiner (Continued)

*Primary Examiner* — Kevin E Weddington
(74) *Attorney, Agent, or Firm* — Wenderoth, Lind & Ponack, L.L.P.

(57) ABSTRACT

The present invention is an aqueous suspension agrochemical composition characterized by containing pyribencarb which is an agrochemically active component, a polyacrylic acid salt, a surfactant, a thickener, and water. The present invention is a method for aerial spraying of an aqueous suspension agrochemical composition, which comprises spraying a diluted solution onto agricultural land or non-agricultural land at an amount of 8 to 32 kg/ha from an aircraft equipped with an agricultural preparation spraying function, the diluted solution being prepared by diluting the aqueous suspension agrochemical composition in water for spraying in an amount of 31 times or less the total amount of the composition on mass basis.

15 Claims, No Drawings

AQUEOUS AGROCHEMICAL SUSPENSION COMPOSITION AND DISPERSAL METHOD THEREFOR

TECHNICAL FIELD

The present invention relates to an aqueous suspension agrochemical composition wherein pyribencarb as an agrochemically active component is suspended and dispersed in water, and a method for spraying the composition. Particularly, the present invention relates to an aqueous suspension agrochemical composition of pyribencarb suitable for aerial spraying and a method for spraying the composition, wherein storage stability is not impaired since particle growth over time is suppressed, and hard cake formation is suppressed even when a spray solution is prepared at a high concentration with a low dilution factor at the time of use.

BACKGROUND ART

Pyribencarb or methyl={2-chloro-5-[(E)-1-(6-methyl-2-pyridylmethoxyimino)ethyl]benzyl}carbamate, which is an agrochemically active component, is a known benzyl carbamate-based bactericide, which is disclosed in Patent Document 1 for the first time. Non Patent Document 1 discloses that it is characterized by having a wide range of control spectrum and exerts an excellent controlling effect on diseases of fruits and vegetables such as gray mold, crown rot, brown rot and the like, caused by various phytopathogenic fungi including ascomycetes.

Dusts, granules, wettable powders, water-dispersible granules, solutions, aqueous suspensions, emulsifiable concentrates and the like are known as forms of agrochemical preparations that have hitherto been put into practical use. Among such agrochemical preparations, an aqueous suspension, i.e., a liquid agrochemical preparation herein particulates of an agrochemically active component relatively insoluble in water are suspended in water, is a widely used form of preparation from the following reasons: there is no dusting at the time of use and there is less concern that a user is exposed to agrochemical preparations; it is easy to weigh; and it is highly safe because it does not use an organic solvent which has adverse effects on the human body and the environment and has low flash point, etc.

In certain aspects of applying the aqueous suspension to agricultural land or non-agricultural land, the aqueous suspension may be applied as it is as a spray solution. However, the method wherein the aqueous suspension may be diluted in a predetermined amount of water to ensure a sufficient liquid volume, and the resulting diluted solution may be applied as a spray solution is generally employed.

Here, the typical methods for applying the spray solution are roughly divided into: ground spraying using a knapsack-type powered sprayer, a boom sprayer, a speed sprayer or the like; and aerial spraying from the air using an aircraft such as a fixed wing machine or a rotary wing machine, equipped with a sprayer. The latter aerial spraying is advantageous in that it can carry out agrochemical treatment in a labor-saving manner on a wide area of agricultural land, etc. However, the amount of spray solution that can be loaded on an aircraft may be inevitably restricted by the load capacity of the aircraft determined by its power performance or the like. Particularly, an unmanned helicopter or a compact unmanned rotary wing machine for spraying agrochemicals, which is commonly referred to as RC (radio control) helicopter, usually has a spray solution amount that can be loaded of about 10 to 24 kg, and thus the amount of the spray solution that can be applied at one flight is limited.

In the case of ground spraying, the aqueous suspension may be added to the predetermined amount of water to prepare a spray solution usually in an amount about 500 to 4,000 times the amount of the aqueous suspension. If it is attempted to apply a large amount of spray solution prepared in this way using the RC helicopter mentioned, above, it is necessary to repeat frequent takeoff and landing and replenishment of spray solution, which is troublesome and non-labor saving. Therefore, for aerial spraying, it is routinely practiced to apply a spray solution usually at about 4 to 32 times of dilution factor, which means much higher concentration than that for ground spraying.

However, with a spray solution of an aqueous suspension prepared at a high concentration with a low dilution factor, a problem which is rarely discussed for a dilute spray solution for ground spraying has become apparent. That is, since the concentration of the agrochemically active component particulates in the diluted solution becomes high, the amount of the agrochemically active component particulates that precipitate considerably increases in proportion to the concentration. Moreover, the deposited layer of the precipitated agrochemically active component particulates form a hard cake in a tank in which the aqueous suspension agrochemical composition is formed or a chemical tank of an aircraft, resulting in a problem of poor dispersion. Since the agrochemically active components which have been converted into a hard cake cannot be discharged from the spray nozzle, not only the desired agrochemical treatment cannot be performed, but also the piping in the spraying machine may be clogged, resulting in a failure. The problem varies in severity depending on the chemical species of the agrochemically active component, and some deposited layers may not become a hard cake. Anyway, pyribencarb has a strong tendency to form a hard cake. Therefore, in order to establish an aqueous suspension of pyribencarb for aerial spraying, technology to formulate preparation while preventing hard cake formation in a spray solution at low dilution factor is required.

As a prior art example of suppressing hard cake formation in a diluted solution of an agrochemical composition, Patent Document 2 discloses a method for preventing solidification of precipitate in a diluted solution of the agrochemical preparation, characterized in that an agrochemical preparation is diluted with water, then a coagulation inhibitor such as aluminum sulfate, polyaluminum chloride, ferric sulfate, carboxymethyl cellulose, poly-acrylic acid ester, polyvinyl alcohol, alginic acid salt, polyvinyl pyrrolidone chitosan is added in, such an amount that generation of aggregates is not observed for at least 15 minutes after addition of the coagulation inhibitor. However, polyacrylic acid salt has not been mentioned. The document also describes that, in the case of a liquid preparation such as a suspension preparation, previously blending above-mentioned coagulation inhibitor in an agrochemical preparation promotes aggregation of the agrochemically active component in the preparation, and results in remarkably inferior inhibition effect on solidification of precipitate compared to the case wherein the coagulation inhibitor is added at the time of dilution. The function of preventing formation of a hard cake at the time of preparing the spray solution of an agrochemical composition at low dilution factor has not been imparted by itself to the agrochemical composition.

Patent Document 3 discloses an aqueous suspension agrochemical preparation characterized in that particulates of a hydrophobic solid agrochemically active component are dispersed in a water by means of a water insoluble solvent which is a good solvent of the agrochemically active component and a surfactant Patent Document 3 also describes that carboxymethyl cellulose, polyvinyl alcohol, polyacrylic acid or a salt thereof, alginic acid salt, polyvinyl pyrrolidone, gum arabic, xanthan gum, gelatin, white carbon, talc, bentonite, clay or the like may be used as a thickener for preventing aggregation or precipitation in the preparation, if desired. The document provides a technique to improve the aggregation/precipitation of solid particles caused by long-term preservation of the aqueous suspension agrochemical preparation of the agrochemically active component having a low melting point. However, the technology includes a water insoluble organic solvent as an essential constitutional requirement and sacrifices the inherent safety which is indicated as an advantage of the aqueous suspension. Moreover, the aqueous suspension agrochemical composition of the invention in the document cannot be expected to suppress formation of hard cake in a spray solution diluted at high concentration with low dilution factor at the time of use. There were no findings on an aqueous suspension agrochemical composition of pyribencarb with performance suitable for aerial spraying.

RELATED ART DOCUMENTS

Patent Documents

PATENT DOCUMENT 1: JP2001-106666A
PATENT DOCUMENT 2: JP2003-34603A
PATENT DOCUMENT 3: JPS63-27401A

Non-Patent Document

NON-PATENT DOCUMENT 1: Kenichi Kida, "Agchem Age", No. 195, NIPPON SODA CO., LTD., December, 2013, pp. 12-17

SUMMARY OF THE INVENTION

Problems to be Solved by the Invention

An object of the present invention is to provide an aqueous suspension agrochemical composition of pyribencarb suitable for aerial spraying and, a method for spraying the composition, wherein hard cake formation is suppressed even when a spray solution is prepared at a high concentration with a low dilution factor at the time of use, without impairing storage stability because particle growth over time is suppressed.

Means for Solving the Problems

As a result of intensive study, the present inventors have found that the above problem can be solved by blending a polyacrylic acid salt into an aqueous suspension agrochemical composition, of pyribencarb, thereby completing the present invention.

The present invention will be described below.

(1) An aqueous suspension agrochemical composition comprising pyribencarb as an agrochemically active component, a polyacrylic acid salt, a surfactant, a thickener, and water.

(2) The aqueous suspension agrochemical composition according to (1), wherein the blending ratio of the pyribencarb is 5 to 40% by mass based on the total amount of the composition.

(3) The aqueous suspension agrochemical composition according to (1) or (2), wherein the molecular weight of the polyacrylic acid salt is 2,500 to 10,000.

(4) The aqueous suspension agrochemical composition according to (1) or (2), wherein the molecular weight of the polyacrylic acid salt is 4,000 to 6,000.

(5) The aqueous suspension agrochemical composition according to any one of (1) to (4), wherein the polyacrylic acid salt is sodium polyacrylate.

(6) The aqueous suspension agrochemical composition according to any one of (1) to (5), wherein the blending ratio of the polyacrylic acid salt is 0.1 to 10% by mass based on the total amount of the composition.

(7) The aqueous suspension agrochemical composition according to any one of (1) to (6), which does not contain a water-insoluble organic solvent.

(8) The aqueous suspension agrochemical composition according to any one of (1) to (7), wherein the viscosity at 20° C. is 200 to 700 mPa·s as measured with a B-type viscometer at rotation speed of 30 rpm.

(9) The aqueous suspension agrochemical composition according to any one of (1) to (7), wherein the viscosity at 20° C. is 250 to 650 mPa·s as measured with a B-type viscometer at rotation speed of 30 rpm.

(10) The aqueous suspension agrochemical composition according to any one of (1) to (9), which is an agrochemical preparation for aerial spraying.

(11) A method, for aerial spraying the aqueous suspension agrochemical composition according to any one of (1) to (10), characterized in that a diluted solution prepared by diluting the aqueous suspension agrochemical composition in water for spraying in an amount 31 times or less the total amount of the composition on mass basis is applied an agricultural land or non-agricultural land at 8 to 32 kg/ha using an aircraft having an agrochemical preparation spraying function.

(12) The method of spraying the aqueous suspension agrochemical composition according to (11), wherein the water for spraying is water or an aqueous liquid in which a predetermined amount of spreading agent and/or another agrochemical preparation is diluted in water.

(13) The method for spraying the aqueous suspension agrochemical composition according to any one of (11) or (12), wherein the molecular weight of the polyacrylic acid salt is 2,500 to 10,000.

(14) The method for spraying the aqueous suspension agrochemical composition according to any one of (11) or (12), wherein the molecular weight of the polyacrylic acid salt is 4,000 to 6,000.

(15) The method for spraying the aqueous suspension agrochemical composition according to any one of (11) to (14), wherein the polyacrylic acid salt is sodium polyacrylate.

(16) The method for spraying the aqueous suspension agrochemical composition according to any one of (11) to (15), wherein the concentration of the polyacrylic acid salt in the diluted solution is 100 to 5,000 ppm.

Effects of the Invention

According to the present invention, the hard cake formation is suppressed even when spray solution is prepared at a high concentration with a low dilution factor at the time of use, without impairing storage stability because particle growth over time is suppressed. Therefore, it is possible to provide an aqueous suspension agrochemical composition of pyribencarb suitable for aerial spraying and a method for spraying the composition.

In addition, using the aqueous suspension agrochemical composition of the present invention eliminates necessity of separately preparing materials for preventing hard cake formation at the time of preparation of spray solution, enabling easy aerial spraying of pyribencarb.

MODE FOR CARRYING OUT THE INVENTION

In this specification, "water for spraying" refers to water which dilutes an aqueous suspension agrochemical composition. The water herein represents pure water or distilled water and may contain trace amounts of agriculturally or industrially acceptable impurities. It is also possible to use drinking water such as mineral water or tap water, and agricultural or industrial water prepared by duly treating groundwater or river water. Further, the water for spraying may be an aqueous liquid in which a predetermined amount of spreading agent and or another agrochemical preparation is diluted in the water mentioned above. In addition, "dilution factor" indicates parts by mass of spray solution prepared by diluting 1 part by mass of the aqueous suspension agrochemical composition. For example, when 1 kg of an aqueous suspension agrochemical composition is diluted with water for spraying to prepare 16 kg of a spray solution, the dilution factor is 16 times in the present specification, the "concentration" of a substance refers to mass concentration unless otherwise specified. In this specification, in reference to the term "molecular weight" of a polymer having a molecular weight distribution, the term refers to a mass average molecular weight.

The aqueous suspension agrochemical composition of the present invention is an aqueous suspension agrochemical composition containing pyribencarb which is an agrochemically active component, a polyacrylic acid salt, a surfactant, a thickener, and water.

In the present invention, the pyribencarb is blended as an agrochemically active component. The blending ratio of the pyribencarb is not particularly limited but is usually in the range of 5 to 40% by mass, preferably 10 to 30% by mass, based on the total amount of the aqueous suspension agrochemical composition.

In the present invention, a polyacrylic acid salt is further added as a hard cake formation inhibitor in a spray solution. The molecular weight of the polyacrylic acid salt is not particularly limited, but those exhibiting almost no thickening effect and having molecular weight of about 2,500 to 10,000 can be suitably used. Especially, those having molecular weight of about 4,000 to 6,000 can be particularly suitably used. A counter cation in a polyacrylic acid salt is not particularly limited. Examples of the polyacrylic acid salt include salts with monovalent cations such as a lithium salt, a sodium salt, a potassium salt, an ammonium salt, a quaternary ammonium salt, a primary to tertiary amine salt. Particularly, the sodium polyacrylate is preferred. The polyacrylic acid salt may be used alone or in combination of two or more.

In the present invention, it is preferable to use the polyacrylic acid salt as a hard cake formation inhibitor, because that makes an aqueous suspension agrochemical composition less likely to become viscous, easy to handle, and further makes the agrochemically active components less likely to aggregate, compared with the case using a coagulation inhibitor employed in the aforementioned prior art documents such as aluminum sulfate, polyaluminum chloride, ferric sulfate, carboxymethyl cellulose, polyacrylic acid ester, polyvinyl alcohol, alginic acid salt, polyvinyl pyrrolidone, chitosan, etc.

In the present invention, the blending ratio of the polyacrylic acid salt is not particularly limited, but it is usually 0.1 to 10% by mass, preferably 0.2 to 8% by mass, particularly preferably 0.5 to 5% by mass, based on the total amount of the aqueous suspension agrochemical composition.

In the aqueous suspension agrochemical composition of the present invention, a surfactant is blended for the purpose of wet-spreading and dispersing a solid component such as pyribencarb. As the surfactant mentioned above, known surfactants can be arbitrarily used. Specific examples of surfactants that can be blended will be listed below, but the present invention is not construed to be limited to these surfactants.

[Nonionic Surfactant]

Polyalkylene glycol, polyalkylene glycol higher fatty acid ester, polyoxyalkylene alkyl ether, polyoxyalkylene alkylaryl ether, polyoxyalkylene arylphenyl ether, sorbitan monoalkylate, acetylene alcohol and acetylene diol as well as an alkylene oxide adduct thereof are included.

[Cationic Surfactant]

Tetraalkyl ammonium salt, alkyl amine and alkyl pyridinium salt are included.

[Anionic Surfactant]

Alkylarylsulfonic acid salt, dialkylsulfonic acid salt, lignin sulfonic acid salt, arylsulfonic acid salt and a condensate thereof, alkylsulfuric acid salt, alkylphosphoric acid salt, alkylarylsulfuric acid salt, alkylaryl phosphoric acid salt, polyoxyalkylene alkyl ether sulfuric acid salt, polyoxyalkylene alkylaryl ether sulfuric acid salt, polyoxyalkylene arylphenyl ether sulfuric acid salt, polyoxyalkylene arylphenyl ether phosphoric acid salt and polycarboxylic acid-type polymer are included.

[Ampholytic Surfactant]

Alkyl betaine, alkyl amine oxide, alkyl imidazolinium betaine amino acid and lecithin are included.

[Other Surfactants]

Silicone-based surfactant and fluorine-based surfactant are included.

The surfactant may be used alone or in combination of two or more. The blending ratio of the surfactant is not particularly limited, but it is usually in the range from 0.1 to 20% by mass, preferably 0.5 to 16% by mass, more preferably 1 to 12% by mass, based on the total amount of the aqueous suspension agrochemical composition.

In the aqueous suspension agrochemical composition of the present invention, a thickener is further blended for the purpose of reduction of liquid phase separation over time and the like. As the thickener, natural polysaccharides such as gum arabic, xanthan gum, guar gum, tamarind gum, pectin, and finely divided mineral matters such as white carbon, talc, bentonite, clay may be suitably used. The natural polysaccharides and finely divided mineral matters are preferable because they are less likely to produce aggregation of pyribencarb in an aqueous suspension agrochemical composition and hardly show increase in viscosity over time compared with substances showing thickening action such as carboxymethyl cellulose, polyvinyl alcohol, a free form of polyacrylic acid, an alginic acid salt and polyvinyl pyrrolidone.

The aforementioned thickener may be used alone or in combination of two more. The blending ratio of the thickener is not particularly limited and varies depending on the types of the thickener to be blended, but it is usually in the range from about 0.05 to 2% by mass based on the total amount of the aqueous suspension agrochemical composition.

In the aqueous suspension agrochemical composition of the present invention, water is blended as a dispersion medium of pyribencarb. The water herein may be of course pure water or distilled water but may contain race amounts of agriculturally or industrially acceptable impurities, it is also possible to use drinking water such as mineral water or tap water, and agricultural or industrial water prepared by duly treating with groundwater or river water. Water also serves as an extender for an aqueous suspension agrochemical composition and its blending ratio is not particularly limited, but when water is insufficient relative to the amount of the pyribencarb, the pyribencarb/water dispersion system in the aqueous suspension agrochemical composition may become unstable. Accordingly, it is preferable to blend water in an amount by mass equal to or more than that, of the pyribencarb.

Auxiliary agents may also be blended into the aqueous suspension agrochemical composition of the present invention as desired. Examples of such an auxiliary agent which is an optional component include an antifreezing agent, an antifoaming agent, a pH adjusting agent, a preservative and the like, and, in addition, known coloring matters such as Pigment Orange 16 or Blue No. 1 Dyes may be added, if desired.

Specific examples of the anti freezing agent include water-soluble substances having relatively low molecular weight typified by urea and common salt; water-soluble polyhydric alcohols typified by propylene glycol, ethylene glycol, diethylene glycol, glycerin, and the like, and a substance known for this usage may be optionally used alone or in combination of two or more.

Specific examples of the antifoaming agent include silicone-based antifoaming agents typified by polyalkyl polysiloxane such as dimethyl polysiloxane, and polyphenyl polysiloxane; fatty acids and metal salts thereof typified by myristic acid and sodium stearate, and a substance known for this usage may be optionally used alone or in combination of two or more.

Examples of the pH adjusting agent include acidic substances typified by sulfuric acid and potassium dihydrogen phosphate; basic substances typified by sodium hydroxide and calcium carbonate; a mixture of a weak acid and a conjugated base thereof, and a mixture of a weak base and a conjugated acid thereof exhibiting buffering capacity in an aqueous solution, and a substance known for this usage may be optionally used alone or in combination of two or more.

Examples of the preservative include parabens, sorbic acid salt, 5-chloro-2-methyl-4-isothiazolin-3-one, 2-bromo-2-propan-1,3-diol, 1,2-benzoisothiazolin-3-one and the like, and a substance known for this usage may be optionally used alone or in combination of two or more.

The aqueous suspension agrochemical composition of the present invention can suppress the formation of a hard cake in a spray solution diluted at low factor at the time of use even if the composition contains no water-insoluble organic solvent. Accordingly, the aqueous suspension agrochemical composition of the present invention does not require water-insoluble organic solvents such as benzene, toluene, xylene, ethylbenzene, styrene, kerosene, dichloromethane, chloroform, carbon tetrachloride, carbon disulfide, liquid paraffin, higher fatty acid, fatty acid ester, aromatic carboxylic acid esters or the like. If desired, a water-insoluble organic solvent may be added to the aqueous suspension agrochemical composition of the present invention, but it is preferable not to blend the water-insoluble organic solvent in consideration of environmental burden and safety to users.

Generally speaking, in an aqueous suspension agrochemical composition, extremely low viscosity results in remarkable liquid phase separation during storage, whereas extremely high viscosity makes it difficult to discharge the composition from a bottle at the time of use. In the present invention, the viscosity range of the aqueous suspension agrochemical composition, within which liquid phase separation during storage is reduced and the composition is allowed to be easily discharged from a bottle during usage, is about 200 to 700 mPa·s, and more preferably about 250 to 650 mPa·s, as measured with a B type viscometer at a rotation speed of 30 rpm, at 20° C.

If desired, an additional agrochemically active component may be added in addition to the aforementioned pyribencarb to prepare an aqueous suspension agrochemical composition of the present invention as a mixed preparation. The additional agrochemically active components may be used alone or in combination so or more. Specific examples of agrochemically active components that can be additionally added will be listed below but are not limited thereto.

[Herbicidal Component]

Ioxynil, aclonifen, acrolein, azafenidin, acifluorfen (including a salt with sodium or the like), azimsulfuron, asulam, acetochlor, atrazine, anilofos, amicarbazone, amidosulfuron, amitrole, aminocyclopyrachlor, aminopyralid, amiprofos-methyl, ametryn, alachlor, alloxydim, isouron, isoxachlortole, isoxaflutole, isoxaben, isoproturon, ipfencarbazone, imazaquin, imazapic (including a salt with amine or the like), imazapyr (including a salt with isopropylamine or the like), imazamethabenz-methyl, imazamox, imazethapyr, imazosulfuron, indaziflam, indanofan, eglinazine-ethyl, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxyfluorfen, oryzalin, orthosulfamuron, orbencarb, cafenstrole, carfentrazone-ethyl, karbutilate, carbetamide, quizalofop-ethyl, quizalofop-P-ethyl, quizalofop-P-tefuryl, quinoclamine, quinclorac, quinmerac, cumyluron, clacyfos, glyphosate (including a salt with sodium, potassium, ammonium, amine, propylamine, isopropylamine, dimethylamine, trimesium or the like), glufosinate (including a salt with amine, sodium or the like), glufosinate-P-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorphthalim, chlorflurenol-methyl, chlorpropham, chlorbromuron, chloroxuron, chlorotoluron, saflufenacil, cyanazine, cyanamide, diuron, diethatyl-ethyl, dicamba (including a salt with amine, diethylamine, isopropylamine, diglycolamine, sodium, lithium or the like), cycloate, cycloxydim, diclosulam, cyclosulfamuron, cyclopyrimorate, dichlobenil, diclofop-P-methyl, diclofop-methyl, dichlorprop, dichlorprop-P, diquat, dithiopyr, siduron, dinitramine, cinidon-ethyl, cinosulfuron, dinoterb, cyhalofop-butyl, diphenamid, difenzoquat, diflufenican, diflufenzopyr, simazine, dimethachlor, dimethametryn, dimethenamid, dimethenamid-P, simetryn, dimepiperate, dimefuron, cinmethylin, swep, sulcotrione, sulfentrazone, sethoxydim, terbacil, daimuron, dalapon, thiazopyr, tiafenacil, thiencarbazone (including a sodium salt, methyl ester or the like), tiocarbazil, thiobencarb, thidiazimin, thifensulfuron-methyl, desmedipham, desmetryne, thenylchlor, tebutam, tebuthiuron, tepraloxydim, tefuryltrione, tembotrione, terbuthylazine, terbutryn, terbumeton, topramezone, tralkoxydim, triaziflam, triasulfuron, triafamone, tri-allate, trietazine, triclopyr, triclopyr-butotyl, trifludimoxazin, tritosulfuron, triflusulfuron-methyl, trifluralin, trifloxysulfuron-sodium, tribenuron-methyl, tolpyralate, naptalam (including a salt with sodium or the like), naproanilide, napropamide, napropamide-M, neburon, norflurazon, vernolate, paraquat, halauxifen-methyl, haloxyfop, haloxyfop-P, haloxyfop-etotyl, halosulfuron-methyl, picloram, picolinafen, bicyclopyrone, bispyribac-sodium, pinoxaden, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pributicarb, pyribenzoxim, pyrimisultan, pyriminobac-methyl, pyroxasulfone, pyroxsulam, phenisopham, fenuron, fenoxasulfone, fenoxaprop-P-ethyl, fenquinotrione, fenthiaprop-ethyl, fentrazamide, phenmedipham, foramsulfuron, butachlor, butafenacil, butamifos, butylate, butenachlor, butralin, butroxydim, flazasulfuron, flamprop (including methyl ester, ethyl ester, isopropyl ester), flamprop-M (including methyl ester, ethyl ester, isopropyl ester), fluazifop-butyl, fluazifop-P-butyl, fluazolate, fluometuron, fluoroglycofen-ethyl, flucarbazone-sodium, fluchloralin, flucetosulfuron, fluthiacet-methyl, flupyrsulfuron-methyl-sodium, flufenacet, flufenpyr-ethyl, flupropanate, flupoxame, flumioxazin, flumiclorac-pentyl, flumetsulam, fluridone, flurtamone, flutroxypyr, flurochloridone, pretilachlor, procarbazone-sodium, prodiamine, prosulfocarb, propaquizafop, propachlor, propazine, propanil, propyzamide, propisochlor, propyrisulfuron, propham, profluazol, propoxycarbazone-sodium, profoxydim, bromacil, brompyrazon, prometryn, prometon, bromoxynil (including an ester such as butyrate, octanoate, or heptanoate), bromofenoxim, bromobutide, florasulam, pethoxamid, benazolin, penoxsulam, heptamaloxyloglucan, beflubutamid, pebulate, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, mecoprop (including a salt, such as sodium salt, potassium salt, isopropylamine salt, triethanolamine salt, dimethylamine salt, or the like), mecoprop-P-potassium, mesosulfuron-methyl, mesotrione, metazachlor, metazosulfuron, methabenzthiazuron, metamitron, metamifop, methiozolin, methyldymuron, metoxuron, metosulam, metobromuron, metobenzuron, metolachlor, metribuzin, mefenacet, monolinuron, molinate, iodosulfuron, iodosulfulon-methyl-sodium, iofensulfuron, iofensulfuron-sodium, lactofen, linuron, lenacil, 2,3,6-TBA (2,3,6-trichlorobenzoic acid), 2,4,5-T(2,4,5-trichlorophenoxyacetic acid), 2,4-D (2,4-dichlorophenoxyacetic acid) (including a salt such as amine salt, diethylamine salt, triethanolamine salt, isopropylamine salt, sodium salt, lithium salt or the like), 2,4-DB (4-(2,4-dichlorophenoxy) butyric acid), AE-F-150944 (Code Number), DNOC (4,6-dinitro-o-cresol) (including a salt such as amine salt, sodium salt or the like), EPTC (S-ethyldipropylthiocarbamate), MCPA (2-methyl-4-chlorophenoxyacetic acid), MCPA-thioethyl, MCPB (2-methyl-4-chlorophenoxybutyric acid) (including a sodium salt, an ethyl ester, or the like), SYP-298 (Code Number), SYP-300 (Code Number), S-metolachlor and TCA (2,2,2-trichloroacetic acid) (including a salt such as sodium salt, calcium salt, ammonia salt, or the like) are included.

[Insecticidal Component]

Acrinathrin, azadirachtin, azamethiphos, azinphos-ethyl, azinphos-methyl, acequinocyl, acetamiprid, aceteprole, acephate, azocyclotin, abamectin, afidopyropen, amidoflumet, amitraz, alanycarb, aldicarb, aldoxycarb, allethrin [including d-cis-trans-isomer, d-trans-isomer], isazophos, isamidofos, isocarbophos, isoxathion, isofenphos-methyl, isoprocarb, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos emamectinbenzoate, endosulfan, empenthrin, oxamyl, oxydemeton-methyl, oxydeprofos, omethoate, cadusafos, kappa-tefluthrin, kappa-bifenthrin, karanjin, cartap, carbaryl, carbosulfan, carbofuran, gamma-BHC, xylylcarb, quinalphos, kinoprene, chinomethionat, coumaphos, cryolite, clothianidin, clofentezine, chromafenozide, chlorantraniliprole, chlorethoxyfos, chlordane, chloropicrin, chlorpyrifos, chlorpyrifos-methyl chlorfenapyr, chlorfenvinphos, chlorfluazuron chlormephos, cyanophos, diafenthiuron, diamidafos, cyantraniliprole, dienochlor, cyenopyrafen, dioxabenzofos, diofenolan, cyclaniliprole, dicrotophos, dichlofenthion, cycloprothrin, dichlorvos, dicloromezotiaz, 1,3-dichloropropene, dicofol, dicyclanil, disulfoton, dinotefuran, dinobuton, cyhalothrin [including gamma-isomer, lambda-isomer], cyphenothrin [including (1R)-trans-isomer], cyfluthrin [including beta-isomer], diflubenzuron, cyflumetofen, diflovidazin, cyhexatin, cypermethrin [including alpha-isomer, beta-isomer, theta-isomer, zeta-isomer], dimethylvinphos, dimefluthrin, dimethoate, silafluofen, cyromazine, spinetoram, spinosad, spirodiclofen, spirotetramat, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, triflumezopyrim, trimethacarb, tolfenpyrad, naled, nitenpyram, novaluron, noviflumoron, Verticillium lecanii, hydroprene, Pasteuriapenerans spore (Pasteuriapenetrans), vamidothion, parathion, parathion-methyl, halfenprox, halofenozide, bioallethrin, bioallethrin S-cyclopentenyl, bioresmethrin, bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin [including (1R)trans-isomer], fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazuron, fluensulfone, sodium fluoroacetate, flucycloxuron, flucythrinate, flusulfamide, fluvalinate [including tau-isomer], flupyradifurone, flupyrazofos, flufiprole, flufenerim, flufenoxystrobin, flufenoxuron, fluhexafon, flubendiamide, flumethrin, protrifenbute, prothiofos, flonicamid, propaphos, propargite, profenofos, broflanilide, profluthrin, propetamphos, propoxur, flometoquin, bromopropylate, hexythiazox, hexaflumuron, Paecilomyces tenuipes, Paecilomyces fumosoroceus, heptafluthrin, heptenophos, permethrin, benclothiaz, bensultap, benzoximate, bendiocarb, benfuracarb, Beauveria tenella, Beauveria bassiana, Beauveria brongniartii, phoxim, phosalone, fosthiazate, fosthietan, phosphamidon, phosmet, polynactin complex (polynactins), formetanate, phorate, malathion, milbemectin, mecarbam, mesulfenfos, methoprene, methomyl, metaflumizone, methamidophos, metham, methiocarb, methidathion, methyl isothiocyanate, methyl bromide, methoxychlor, methoxyfenozide, methothrin, metofluthrin, methoprene, metolcarb, mevinphos, meperfluthrin, Monacrosporium phymatophagum, monocrotophos, momfluorothrin, litlure-A, litlure-B, aluminium phosphide, zinc phosphide, hydrogen phosphide (phosphine), lufenuron, rescalure, resmethrin, lepimectin, rotenone, fenbutatin oxide, calcium cyanamide (calcium cyanide), nicotine sulfate, (Z)-11-tetradecenyl=acetate, (Z)-11-hexadecenal, (Z)-11-hexadecenyl=acetate, (Z)-9,12-tetradecadienyl=acetate, (Z)-9-tetradecen-1-ol, (Z,E)-9,11-tetradecadienyl=acetate, (Z,E)-9,12-tetradecadienyl=acetate, *Bacillus popilliae, Bacillus subtillis, Bacillus sphaericus, Bacillus thuringiensis* subsp. Aizawai, *Bacillus thuringiensis* subsp. Israelensis, *Bacillus thuringiensis* subsp. Kurstaki, *Bacillus thuringiensis* subsp. Tenebrionis, Bt protein (Cry1Ab, Cry1Ac, Cry1Fa, Cry2Ab, mCry3A, Cry3Ab, Cry3Bb, Cry34/35Abl), CL900167 (Code Number), DCIP (bis-(2-chloro-1-methylethy)ether), DDT (1,1,1-trichloro-2,2-bis(4-chlorophenyl)ethane), DEP (dimethyl-2,2,2-trichloro-1-hydroxyethylphosphonate), DNOC (4,6-dinitro-o-cresol), DSP (O,O-diethyl-O-[4-(dimethylsulfamoyl)phenyl]-phosphorothioate), EPN (O-ethyl-O-4-(nitrophenyl)phenylphosphorothioate, nuclear polyhedrosis visur occlusion body, NA-85 (Code Number), NA-89 (Code Number), NC-515 (Code Number), RU15525 (Code Number), ZDI-2501 (Code Number), XMC, Z-13-icosen-10-one, ZX18901 (Code Number) and ME5382 are included.

[Antibacterial Component]

Azaconazole, acibenzolar-S-methyl, azoxystrobin, anilazine, amisulbrom, ametoctradin, aldimorph, isotianil, isopyrazam, isofetamid, isoprothiolane, ipconazole, iprodione, iprovalicarb, iprobenfos, imazalil, iminoctadine albesilate (iminoctadine-trialbesilate), iminoctadine-triacetate, imibenconazole, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxyquinoline copper (oxine-copper), oxytetracycline, oxpoconazole-fumarate, oxolinic acid, copper octanoate (copper dioctanoate), octhilinone, ofurace, orysastrobin, o-phenylphenol, kasugamycin, captafol, carpropamid, carbendazim, carboxin, carvone, quinoxyfen, chinomethionat, captan, quinconazole, quintozene, guazatine, cufraneb, coumoxystrobin, kresoxim-methyl, clozylacon, chlozolinate, chlorothalonil, chloroneb, cyazofamid, diethofencarb, diclocymet, dichlofluanid, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, ziram, silthiofam, streptomycin, spiroxamine, sedaxane, zoxamide, dazomet, tiadinil, thiabendazole, thiram, thiophanate, thiophanate-methyl, thifluzamide, tecnazene, teclofialam, tetraconazole, debacarb, tebuconazole, tebufloquin, terbinafine, dodine, dodemorph, triadimenol, triadimefon, triazoxide, trichlamide, triclopyricarb, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Bacillus subtilis* (strain: QST 713), validamycin, valifenalate, picarbutrazox, bixafen, picoxystrobin, bitertanol, binapacryl, biphenyl, piperalin, hymexazol, pyraoxystrobin, pyraclostrobin, pyraziflumid, pyrazophos, pyrametostrobin, pyriofenone, pyrisoxazole, pyrifenox, pyributicarb, pyrimethanil, pyroquilon, vinclozolin, ferbam, famoxadone, phenazine oxide, fenamidone, fenaminstrobin, fenarimol, fenoxanil, ferimzone, fenpiclonil, fenpyrazamine, fenbuconazole, fenfuram, fenpropidin, fenpropimorph, fenhexamid, folpet, phthalide, bupirimate, fuberidazole, blasticidin-S, furametpyr, furalaxyl, furancarboxylic acid, fluazinam, fluoxastrobin, fluopicolide, fluopyram, fluoroimide, fluxapyroxad, fluquinconazole, furconazole, furconazole-cis, fludioxonil, flusilazole, flusulfamide, flutianil, flutolanil, flutriafol, flufenoxystrobin, flumetover, flumorph, proquinazid, prochloraz, procymidone, prothiocarb, prothioconazole, bronopol, propamocarb-hydrochloride, propiconazole, propineb, probenazole, bromuconazole, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (alminium, calcium, sodium), polyoxin, polycarbamate, Bordeaux mixture, mancozeb, mandipropamid, mandestrobin, maneb, myclobutanil, mineral oils, mildiomycin, methasulfocarb, metam, metalaxyl, metalaxyl-M, metiram, metconazole, metominostrobin, metrafenone, mepanipyrim, meptyldinocap, mepronil, iodocarb, laminarin, phosphorous acid and salts, copper oxychloride, silver, cuprous oxide, copper hydroxide, potassium bicarbonate, sodium bicarbonate, sulfur, oxyquinoline sulfate, copper sulfate, (3,4-dichloroisothiazol-5-yl)methyl 4-(tert-butyl)benzoate (Chemical Name, CAS Registered Number: 1231214-23-5), 3-((3,4-dichloroisothiazol-5-yl) methoxy)benzo[d]isothiazol-1,1-dioxide (Chemical Name, CAS Registered Number: 957144-77-3), BAF-045 (Code Number), BAG-010 (Code Number), DBEDC (dodecylbenzenesulfonic acid bisethylenediamine copper complex salt [II]), MIF-1002 (Code Number), TPTA (fentin acetate), TPTC (triphenyltin chloride), TPTH (triphenyltin hydroxide) and nonpathogenic *Erwinia carotovora* are included.

[Active Component for Plant Growth Regulation]

1-Methylcyclopropene, 1-naphthylacetamide, 2,6-diisopropylnaphthalene, 4-CPA (4-chlorophenoxyacetic acid), benzylaminopurine, ancymidol, aviglycine, carvone, chlormequat cloprop, cloxyfonac, cloxyfonac-potassium, cyclanilide, cytokinins, daminozide, dikegulac, dimethipin, ethephon, epocholeone, ethychlozate, flumetralin, flurenol, flurprimidol, forchlorfenuron, gibberellins, inabenfide, indole acetic acid, indole butyric acid, maleic hydrazide, mefluidide, mepiquat chloride, n-decanol, paclobutrazol, prohexadione-calcium, prohydrojasmon, sintofen, thidiazuron, triacontanol, trinexapac-ethyl, uniconazole, uniconazole-P, -4-(24-oxo-phenylethyl)aminobutyric acid (Chemical Name, CAS Registered Number: 1083-55-2) and calcium peroxide are included.

Among these additional agrochemically active components, MCPB, azimsulfuron, imazosulfuron, etobenzanid, oxaziclomefone, cafenstrole, carfentrazone-ethyl, glyphosate isopropylamine salt, glyphosate potassium salt, glufosinate-P-sodium, clomeprop, cyhalofop-butyl, dimethametryn, simetryn, daimuron, tefuryltrione, halosulfuron-methyl, pyraclonil, pyrazoxyfen, pyrazosulfuron-ethyl, pyrazolynate, pyriftalid, pyributicarb, pyrimisulfan, pyriminobac-methyl, fentrazamide, flucetosulfuron, pretilachlor, propyrisulfuron, bromobutide, penoxsulam, bensulfuron-methyl benzobicyclon, benzofenap, pentoxazone, benfuresate, mesotrione, metazosulfuron, mefenacet, molinate, fenitrothion, acetamiprid, acephate, imidacloprid, indoxacarb, ethiprole, etofenprox, clothianidin, chromafenozide, chlorantraniliprole, dinotefuran, cypermethrin, silafluofen, thiacloprid, thiamethoxam, thiodicarb, tebufenozide, teflubenzuron, pyridalyl, buprofezin, flubendiamide, permethrin, methoxyfenozide, nuclear polyhedrosis visur occlusion body, chlorothalonil, azoxystrobin, isoprothiolane, iminoctadine-albesilate, iminoctadine-acetate, imibenconazole, kasugamycin, cyazofamid, diclocymet, simeconazole, cymoxanil, thiophanate-methyl, tetraconazole, tebuconazole, tricyclazole, tolclofos-methyl, *Bacillus subtilis*, validamycin, pyroquilon, famoxadone, fenoxanil, ferimzone, phthalide, furametpyr, flutolanil, procymidone, propiconazole, probenazole, pencycuron, mancozeb, metalaxyl, metconazole, metominostrobin, mepronil, nonpathogenic Erwinia carotovora, calcium peroxide, trinexapac-ethyl, paclobutrazol, and prohexadione-calcium are preferably used because they have proven track record as agrochemical preparations for aerial spraying and may be added to the aqueous suspension agrochemical composition of the present invention with good compatibility.

When an additional agrochemically active component is blended in addition to the pyribencarb into the aqueous suspension agrochemical composition of the present invention, the blending ratio of the agrochemically active components including the pyribencarb is not particularly limited, but it is usually 10 to 50% by mass, preferably 15 to 45% by mass, based on the total amount of the aqueous suspension agrochemical compositions.

In addition, a phytotoxicity reducing agent may be blended into the aqueous suspension agrochemical composition of the present invention, if desired. Specific examples of phytotoxicity reducing agents that can be blended will be listed below, bat the present invention is not construed to be limited to these phytotoxicity reducing agents.

[Phytotoxicity Reducing Agent]

Isoxadifen isoxadifen-ethyl, oxabetrinil, cloquintcetmexyl, cyometrinil, dichlormid, dicyclonon cyprosulfamide, 1,8-naphthalic anhydride, fenchlorazole-ethyl, fenclorim, furilazole, fluxofenim, flurazole, benoxacor, mefenpyr, mefenpyr-ethyl, mefenpyr-diethyl, lower alkyl-substituted benzoic acid, AD-67 (4-dichloroacetyl-1-oxa-4-azaspiro[4,5]decane), DKA-24 (N1,N2-diallyl-N2-dichloroacetylglycinamide), MG-191 (2-dichloromethyl-2-methyl-1,3-dioxane), MON4660 (Code Number), N-(2-methoxybenzoyl)-4-[(methylaminocarbonyl)amino]benzenesulfonamide (Chemical Name, CAS Registered Number: 129531-12-0), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine) and TI-35 (Code Number) are included.

The phytotoxicity reducing agent may be used alone or in combination of two or more. When these phytotoxicity reducing agents are blended in the aqueous suspension agrochemical composition of the present invention, the blending ratio of phytotoxicity reducing agent is not particularly limited, but it is usually 1 to 40% by mass, preferably 2 to 30% by mass, more preferably 3 to 20% by mass, based on the total amount of the aqueous suspension agrochemical composition.

As the pryibencarb and additional agrochemically active components, a pure product or a technical product may be directly used. Alternatively, they may be used in the form of reservoir type microcapsules containing the agrochemically active components coated with wall materials or in the form of monolithic type microcapsules in which the agrochemically active components are dispersed in the core of matrix. Application of formulation pretreatment technique of agrochemically active component is not particularly limited and known methods and materials may be optionally used as desired.

The amount of the aqueous suspension agrochemical composition of the present invention to be applied varies depending on the target disease, occurrence tendency, extent of damage, environmental conditions, etc. For example, it may be appropriately selected so that the amount of pyribencarb should be 1 to 10,000 g/ha, preferably 10 to 1,000 g/ha. The aqueous suspension agrochemical composition of the present invention can control plant diseases caused by fungi belonging to Oomycota, Ascomycota, Basidiomycota, and Deuteromycota according to the above application embodiment. Specific plant pathogenic bacteria that can be controlled will be listed below but are not limited to them.

[Plant Pathogenic Microbe]

Pseudoperonospora such as Pseudoperonospora cubensis; Venturia such as Venturia inaequalis; Erysiphe such as Erysiphe graminis; Pyricularia such as Pyricularia oryzae; Botrytis such as Botrytis cinerea; Rhizoctonia such as Rhizoctonia solani; Puccinia such as Puccinia recondite; Septoria such as Septoria nodorum; and Sclerotinia such as Sclerotinia sclerotiorum are included.

The method for producing the aqueous suspension agrochemical composition of the present invention is not particularly limited, but a method wherein pyribencarb, a polyacrylic acid salt, a surfactant, a thickener, water and optionally other optional ingredients are mixed, wet-pulverized and, stirred at high speed with a grinding medium such as glass heads, ceramic beads, stainless beads or the like to obtain an aqueous suspension agrochemical composition is typically mentioned. Alternatively, for the purpose of, for example, improving the efficiency of the pulverization step, all of the pyribencarb and a part of the remaining raw materials are mixed and wet-pulverized to produce slurry of pyribencarb, subsequently the remaining raw materials may be added to the slurry and mixed to obtain an aqueous suspension agrochemical composition. Alternatively, the pyribencarb may be dry-pulverized using means such as impact pulverization, air flow pulverization or the like, and the dry-pulverized pyribencarb may be added to a mixture comprising a polyacrylic acid salt, a surfactant, a thickener, and water as well as other optional component if desired, and allowed to disperse to provide an aqueous suspension agrochemical composition.

Whichever manufacturing method is employed, it is preferred to finely pulverize the pyribencarb in order to attain favorable dispersion of the pyribencarb in an aqueous suspension agrochemical composition or in a diluted solution at the time of use. The particle size of the pyribencarb particles attained during the pulverization step is preferably from about 0.2 to 10 μm, more preferably from about 0.5 to 6 μm as volume average particle size. If the size of a pyribencarb particle in an aqueous suspension agrochemical composition exceeds 10 μm, liquid phase separation during storage may become conspicuous, and the pyribencarb particles precipitate quickly even in a diluted solution, resulting in difficulty in obtaining a uniform spray solution. The volume average particle size of the pyribencarb particles can be measured, for example, by a laser diffraction method or a measuring apparatus using this method as a measuring principle.

The aqueous suspension agrochemical composition of the present invention thus prepared is preferred as an, agrochemical preparation for aerial spraying. "Agrochemical preparation for aerial spraying" refers to an agrochemical preparation which is registered to be used by "aerial spraying" or by "spraying with an unmanned helicopter" and the means for application is described on an agrochemical label, from the standpoint of the domestic law in Japan. It is possible for the preparation to be entered in the agrochemical register if it provides good results in efficacy test and phytotoxicity test. However, the spray solution which is prepared at low dilution factor, i.e. generally about 4 to 32 times is desired to have good stability at high concentration based on the performance demand of users, such low dilution factor being characteristic for aerial spraying. Otherwise, it shall be impractical as an agrochemical preparation for aerial spraying.

The method for aerial spraying of the present invention is characterized in that a diluted solution prepared by diluting the aqueous suspension agrochemical composition in water for spraying in an amount of 31 times or less the total mass of the composition on mass basis is applied on agricultural land or non-agricultural land at 2 to 150 kg/ha, preferably 8 to 32 kg/ha using an aircraft having an agrochemical preparation spraying function.

In the case of aerially spraying the aqueous suspension agrochemical composition of the present invention, the aqueous suspension agrochemical composition may be firstly diluted with water for spraying usually at a dilution factor of 4 to 32 times to prepare a spray solution. That is, the amount of water for spraying is usually 3 to 31 times the total amount of the aqueous suspension agrochemical composition on mass basis.

However, in actual use of agrochemical preparations, two or more agrochemical preparations may be mixed in the same spray solution and sprayed at the same time. Such operation is known as combined application (hereinafter also referred to as "combine application" in this specification). In this case, however, the aqueous suspension agrochemical composition, of the present invention may be diluted with water for spraying by dilution factor of less than 4 times. That is, in the case of combined application oldie aqueous suspension agrochemical composition of the present invention and another agrochemical preparation, when the aqueous suspension agrochemical composition of the present invention is to be diluted in a water for spraying, and then another agrochemical preparations to be diluted to a predetermined amount, the aqueous suspension agrochemical composition of the present invention may be diluted temporarily at dilution factor of less than 4 times in expectation of increase in the total liquid amount due to subsequent addition of another agrochemical preparation.

Therefore, the aqueous suspension agrochemical composition of the present invention may be diluted with water for spraying in the amount of 31 times or less the total amount of the composition on mass basis according to the actual usage requirement to prepare a spray solution which can be used for aerial spraying.

A polyacrylic acid salt strongly inhibits formation of a pyribencarb hard cake in the spray solution. The concentration of the polyacrylic acid salt in a spray solution is not limited, and an effect of reducing hard cake formation may be observed in an amount as small as about 100 ppm. Although higher concentrations of the polyacrylic acid salt may more strongly inhibit the formation of the hard cake, the concentration is desirably up to about 5,000 ppm considering economy. Therefore, the preferred concentration of the polyacrylic acid salt of the present invention in the spray solution is in the range from 100 to 5,000 ppm, more preferably 200 to 3,000 ppm. It is needless to say that the aqueous suspension agrochemical composition is designed so that the polyacrylic acid salt should have the above effective concentration in the spray solution, in the case of adding the polyacrylic acid salt to the aqueous suspension agrochemical composition, considering the dilution factor at the time of use of the composition.

The spray solution prepared as described above is placed in an agrochemical liquid tank in an agrochemical spraying device mounted on an aircraft, and the spray solution is sprayed from the aircraft flying over the agricultural land or non-agricultural land while spraying the spray solution. In this way, aerial spraying of the aqueous suspension agrochemical composition of the present invention is carried out. Examples of an aircraft used for the method for spraying mentioned above may include a fixed wing aircraft such as a small light aircraft called Cessna plane, a rotary wing machine such as a manned helicopter or an unmanned helicopter, and a tilt rotor machine that combines both characteristics. In particular, a small unmanned helicopter specialized for spraying agrochemicals can be suitably used. In the case of aerial spraying of agrochemicals from an aircraft, the volume of the spray solution is usually 2 to 150 kg/ha, more typically 8 to 32 kg/ha.

The aqueous suspension agrochemical composition of the present invention can also be applied in the form of a tank mix when preparing a spray solution. In particular, the polyacrylic acid salt used in the present invention is an indispensable element for the aqueous suspension agrochemical composition of the present invention as a hard cake formation inhibitor which can be ready-mixed, but it may also exhibit the desired effect as a tank-mixed form. Moreover, a coagulation inhibitor used in the prior art documents described above such as aluminum sulfate, polyaluminum chloride, ferric sulfate, carboxymethyl cellulose, polyacrylic acid ester, polyvinyl alcohol, alginic acid salt, polyvinyl pyrrolidone and chitosan may be blended into the aqueous suspension agrochemical composition of the present invention as an additional auxiliary agent so long as it is in a tank-mixed form.

In addition, in the aqueous suspension agrochemical composition containing pyribencarb, blending polyoxyalkylene alcohol or polyoxyethylene-polyoxypropylene block copolymer as a surfactant increases viscosity of the aqueous suspension agrochemical composition and may cause additional increase and/or particle growth in viscosity during storage although controlling effect may be enhanced. In order to avoid such risks, it is generally required to take measures, for example, by using another specific surfactant at the same time. For the purpose, in the case where the polyoxyalkylene alcohol or polyoxyethylene-polyoxypropylene block copolymer mentioned above is used together with an aqueous suspension agrochemical composition containing pyribencarb, it is convenience to use a polyoxyalkylene alcohol or polyoxyethylene-polyoxypropylene block copolymer as a tank-mix during preparation of a spray solution of the aqueous suspension agrochemical composition.

EXAMPLES

The present invention will be described in detail in Examples. The present invention is not intended to be limited to these Examples. In the following Examples, parts means parts by mass. A volume average particle size is a value measured using a laser diffraction scattering type particle size distribution meter (trade name "Laser Micron Sizer LMS-2000e" manufactured by SEISHIN ENTERPRISE CO., LTD). The viscosity is a value obtained by measurement of a sample at 20° C. and 30 rpm using a B-type viscometer (trade name "TVB-10-M" manufactured by TOKI SANGYO CO. LTD.).

Example 1

Pyribencarb (20 parts), sodium polyacrylate having molecular weight of 5,000 (0 parts), polyoxyalkylene arylphenyl ether phosphoric acid salt (4 parts), propylene glycol (10 parts), xanthan guru (0.28 parts), polyalkyl polysiloxane (0.02 parts) and water (65.5 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 572 mPa·s.

Example 2

Pyribencarb (20 parts), sodium polyacrylate having molecular we fight of 5,000 (0.5 parts), polyoxyalkylene arylphenyl ether phosphoric acid salt (4 parts), propylene glycol (10 parts), xanthan gum (0.28 parts), polyalkyl polysiloxane (0.02 parts) and water (65.2 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 601 mPa·s.

Example 3

Pyribencarb (20 parts), sodium polyacrylate having molecular weight of 5,000 (2 parts), polyoxyalkylene arylphenyl ether phosphoric acid salt (4 parts), propylene glycol (10 parts), xanthan gum (0.28 parts), polyalkyl polysiloxane (0.02 parts) and water (63.7 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 584 mPa·s.

Example 4

Pyribencarb (20 parts), sodium polyacrylate having molecular weight of 5,000 (5 parts), polyoxyalkylene arylphenyl ether phosphoric acid salt (4 parts), propylene glycol (10 parts), xanthan gum (0.28 parts), polyalkyl polysiloxane (0.02 parts) and water (60.7 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 606 mPa·s.

Example 5

Pyribencarb (20 parts), sodium polyacrylate having molecular weight of 5,000 (0.5 parts), polyoxyalkylene arylphenyl ether sulfuric acid salt (1.6 parts), polyalkylene glycol (1.6 parts), ethylene glycol (7.4 parts), liquid paraffin (8 parts), xanthan gum (0.25 parts), polyalkyl polysiloxane (0.02 parts) and water (60.63 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 298 mPa·s.

Example 6

Pyribencarb (20 parts), sodium polyacrylate having molecular weight of 5,000 (0.5 parts), polyoxyalkylene arylphenyl ether sulfuric acid salt (4 parts), propylene glycol (15 parts), xanthan gum (0.3 parts), polyalkyl polysiloxane (0.02 parts) and water (60.18 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 631 mPa·s.

Comparative Example 1

Pyribencarb (20 parts), polyoxyalkylene arylphenyl ether phosphoric acid salt (4 parts), propylene glycol (10 parts), xanthan gum (0.28 parts), polyalkyl polysiloxane (0.02 parts) and water (65.7 parts) were mixed and wet-pulverized to an average particle size of 3 µm as a volume average particle size, to obtain an aqueous suspension agrochemical composition containing 20% by mass of the pyribencarb. The viscosity of thus obtained aqueous suspension agrochemical composition was 565 mPa·s.

Comparative Example 2

Pyribencarb (20 parts), alginic acid (0.2 parts), polyoxyalkylene arylphenyl ether phosphoric acid salt (4 parts), propylene glycol (10 parts), xanthan gum (0.28 parts), polyalkyl polysiloxane (0.02 parts) and water (65.5 parts) were mixed and wet-pulverized to an average particle size of 3 µm as a volume average particle size, to obtain an aqueous suspension agrochemical composition containing 20% by mass of the pyribencarb. The thus obtained aqueous suspension agrochemical composition had viscosity of 814 mPa·s, poor fluidity, and somewhat difficulty in packing into and discharging from a bottle.

Comparative Example 3

Pyribencarb (20 parts), alginic acid (0.5 parts), polyoxyalkylene arylphenyl ether phosphoric acid salt (4 parts), propylene glycol (10 parts), xanthan gum (0.28 parts), polyalkyl polysiloxane (0.02 parts) and water (65.2 parts) were mixed and wet-pulverized to an average particle size of 3 µm as a volume average particle size, to obtain an aqueous suspension agrochemical composition containing 20% by mass of die pyribencarb. The thus obtained aqueous suspension agrochemical composition exhibited high viscosity of 1,593 mPa·s, extremely poor fluidity, and had great difficulty in packing into and discharging from a bottle.

Comparative Example 4

Pyribencarb (20 parts), polyoxyalkylene arylphenyl ether phosphoric acid salt (4 parts), propylene glycol (10 parts), xanthan gum (0.33 parts), polyalkyl polysiloxane 0.02 parts) and water (65.65 parts) were mixed and wet pulverized to an average particle size of 3 µm as a volume average particle size, to obtain an aqueous suspension agrochemical composition containing 20% by mass of the pyribencarb. Thus obtained aqueous suspension agrochemical composition exhibited high viscosity of 1,024 mPa·s, extremely poor fluidity, and had great difficulty in packing into and discharging from a bottle.

Comparative Example 5

Pyribencarb (20 parts), carboxymethyl cellulose 0.5 parts), polyoxyalkylene arylphenyl ether phosphoric acid, salt (4 parts), propylene glycol (10 parts), xanthan gum (0.28 parts), polyalkyl polysiloxane (0.02 parts) and water (65.2 parts) were mixed and wet-pulverized to an average particle size of 3 μm as a volume average particle size, to obtain an aqueous suspension agrochemical composition containing 20% by mass of the pyribencarb. The thus obtained aqueous suspension agrochemical composition exhibited high viscosity of 1,810 mPa·s, extremely poor fluidity, and had great difficulty in packing into and discharging from a bottle.

Comparative Example 6

Pyribencarb (20 parts), polyaluminum chloride (0.5 parts), polyoxyalkylene arylphenyl ether phosphoric acid salt (4 parts), propylene glycol (10 parts), xanthan gum (0.28 parts), polyalkyl poly siloxane (0.02 parts) and water (65.2 parts) were mixed and wet-pulverized to an average particle size of 3 μm as a volume average particle size. Pyribencarb aggregated immediately after pulverization, resulting in aggregated particles larger than 10 μm. Thus, practicable aqueous suspension agrochemical composition could not be obtained.

Test Example 1

Aqueous suspension agrochemical compositions of Examples 1 to 6 and Comparative Examples 1 to 5 (6.25 g) were taken in a 100 mL stoppered measuring cylinder, to which was added hard water (3 degree) adjusted to 2° C. to make the total amount 100 g (dilution factor, 16). The solution was shaken and mixed thoroughly to prepare a homogeneous diluted solution. The measuring cylinder was allowed to stand at a constant temperature of 20° C., and after 24 hours, the thickness of the layer deposited at the bottom was recorded. Thereafter, the measuring cylinder was inverted at 30 rpm, and the light permeability of the bottom surface was observed every 5 inversion operations, and the number of inversion operations required until the deposited layer was re dispersed was recorded. The results are shown in Table 1.

TABLE 1

| | Concentration of polyacrylic acid salt [ppm] | Thickness of deposited layer [mm] | Number of inversion operations required for re-dispersion [times] |
|---|---|---|---|
| Example 1 | 125 | 1 | 11-15 |
| Example 2 | 312.5 | 3 | 6-10 |
| Example 3 | 1250 | 3 | 1-5 |
| Example 4 | 3125 | 3 | 1-5 |
| Example 5 | 312.5 | 3 | 6-10 |
| Example 6 | 312.5 | 3 | 6-10 |
| Comparative Example 1 | 0 | 2 | 50 or more |
| Comparative Example 2 | 0 | 3 | 11-15 |
| Comparative Example 3 | 0 | 3 | 11-15 |
| Comparative Example 4 | 0 | 2 | 50 or more |
| Comparative Example 5 | 0 | 2 | 50 or more |

Test Example 2

The aqueous suspension agrochemical compositions of Examples 1 to 6 and Comparative Examples 2 to 3 were packaged in capped glass bottles and stored in a constant-temperature unit at 54° C. for 14 days. Thereafter, the viscosity of the aqueous suspension agrochemical composition and the volume average particle size of pyribencarb particles were measured in the same manner as that performed immediately after production. The results are shown in Table 2.

TABLE 2

| | Viscosity [mPa·s] | | Volume average particle size [μm] | |
|---|---|---|---|---|
| | Immediately after production | After storage | Immediately after production | After storage |
| Example 1 | 572 | 575 | 3 | 3 |
| Example 2 | 601 | 596 | 3 | 3 |
| Example 3 | 584 | 577 | 3 | 3 |
| Example 4 | 606 | 610 | 3 | 3 |
| Example 5 | 298 | 302 | 3 | 3 |
| Example 6 | 631 | 633 | 3 | 3 |
| Comparative Example 2 | 814 | 1098 | 3 | 7 |
| Comparative Example 3 | 1593 | 1839 | 3 | 11 |

The invention claimed is:

1. An aqueous suspension agrochemical composition comprising pyribencarb as an agrochemically active component, a polyacrylic acid salt, a surfactant, a thickener, and water,
wherein the viscosity of the composition at 20° C. is 200 to 700 mPa·s as measured with a B-type viscometer at rotation speed of 30 rpm.

2. The aqueous suspension agrochemical composition according to claim 1, wherein the blending ratio of the pyribencarb is 5 to 40% by mass based on the total amount of the composition.

3. The aqueous suspension agrochemical composition according to claim 1, wherein the molecular weight of the polyacrylic acid salt is 2,500 to 10,000.

4. The aqueous suspension agrochemical composition according to claim 1, wherein the molecular weight of the polyacrylic acid salt is 4,000 to 6,000.

5. The aqueous suspension agrochemical composition according to claim 1, wherein the polyacrylic acid salt is sodium polyacrylate.

6. The aqueous suspension agrochemical composition according to claim 1, wherein the blending ratio of the polyacrylic acid salt is 0.1 to 10% by mass based on the total amount of the composition.

7. The aqueous suspension agrochemical composition according to claim 1, which does not contain a water-insoluble organic solvent.

8. The aqueous suspension agrochemical composition according to claim 1, wherein the viscosity at 20° C. is 250 to 650 mPa·s as measured with a B-type viscometer at rotation speed of 30 rpm.

9. The aqueous suspension agrochemical composition according to claim 1, which is an agrochemical preparation for aerial spraying.

10. A method for aerial spraying the aqueous suspension agrochemical composition according to claim 1, comprising diluting the aqueous suspension agrochemical composition in water for spraying in an amount 31 times or less of the total amount of the composition on mass basis to obtain a diluted solution, and applying the diluted solution on agricultural land or non-agricultural land at 8 to 32 kg/ha using an aircraft having an agrochemical preparation spraying function.

11. The method for spraying the aqueous suspension agrochemical composition according to claim 10, wherein the water for spraying is water or an aqueous medium in which a predetermined amount of a spreading agent and/or another agrochemical preparation is dissolved in water.

12. The method for spraying the aqueous suspension agrochemical composition according to claim 10, wherein the molecular weight of the polyacrylic acid salt is 2,500 to 10,000.

13. The method for spraying the aqueous suspension agrochemical composition according to claim 10, wherein the molecular weight of the polyacrylic acid salt is 4,000 to 6,000.

14. The method for spraying the aqueous suspension agrochemical composition according to claim 10, wherein the polyacrylic acid salt is sodium polyacrylate.

15. The method for spraying the aqueous suspension agrochemical composition according to claim 10, wherein the concentration of the polyacrylic acid salt in the diluted solution is 100 to 5,000 ppm.

* * * * *